United States Patent
Tazi

(10) Patent No.: US 7,018,354 B2
(45) Date of Patent: Mar. 28, 2006

(54) LIPOSUCTION DEVICES AND METHODS AND SURROUNDING ASPIRATION SYSTEMS AND METHODS

(76) Inventor: El Hassane Tazi, 43, Rue Sebou, Gauthier (MA)

( * ) Notice: Subject to any disclaimer, the term of this patent is extended or adjusted under 35 U.S.C. 154(b) by 549 days.

(21) Appl. No.: 10/289,569

(22) Filed: Nov. 7, 2002

(65) Prior Publication Data
US 2003/0088235 A1    May 8, 2003

Related U.S. Application Data

(60) Provisional application No. 60/337,045, filed on Nov. 8, 2001.

(51) Int. Cl.
*A61B 17/20* (2006.01)
*A61B 17/32* (2006.01)

(52) U.S. Cl. .................. 604/22; 604/35; 604/902; 606/169; 606/170; 606/171

(58) Field of Classification Search ............... 604/22, 604/35, 73, 902; 601/2; 606/169–171
See application file for complete search history.

(56) References Cited

U.S. PATENT DOCUMENTS

| | | | |
|---|---|---|---|
| 4,428,748 A * | 1/1984 | Peyman et al. ............ 604/22 |
| 4,886,491 A | 12/1989 | Parisi et al. |
| 5,123,903 A | 6/1992 | Quaid et al. |
| 5,236,414 A * | 8/1993 | Takasu ...................... 604/22 |
| 5,244,458 A * | 9/1993 | Takasu ...................... 604/22 |
| 5,419,761 A | 5/1995 | Narayanan et al. |
| 5,514,086 A | 5/1996 | Parisi et al. |
| 5,591,184 A * | 1/1997 | McDonnell et al. ........ 606/167 |
| 5,722,980 A | 3/1998 | Schulz et al. |
| 6,033,375 A | 3/2000 | Brumbach |
| 6,159,176 A | 12/2000 | Broadwin et al. |
| 6,270,471 B1 | 8/2001 | Hechel et al. |
| 6,322,583 B1 * | 11/2001 | Tu et al. ..................... 607/96 |
| 6,336,925 B1 | 1/2002 | Malak |
| 6,368,299 B1 | 4/2002 | Cimino |

(Continued)

FOREIGN PATENT DOCUMENTS

| WO | WO-93/14708 | 8/1993 |
| WO | WO-99/13783 | 3/1999 |

OTHER PUBLICATIONS

International search report for PCT/IB02/04926.*

*Primary Examiner*—Tatyana Zalukaeva
*Assistant Examiner*—M. G. Bogart
(74) *Attorney, Agent, or Firm*—Blakely, Sokoloff, Taylor & Zafman LLP

(57) ABSTRACT

Liposuction devices and methods and surrounding aspiration systems and methods that reduce the chances of burning and necrosis. The devices include an evacuation tube surrounding an ultrasonic probe, including the distal end thereof to define a liquefaction and/or rupture chamber. The evacuation tube has one or more openings in the distal end through which tissue such as fatty tissue may enter for rupture/liquefaction therein. Containing the ultrasonic probe within the evacuation tube avoids any possible contact with surrounding tissue other than tissue that gets drawn into the liquefaction and/or rupture chamber. The size of the liquefaction and/or rupture chamber may be variable by adjustment of the axial position of the evacuation tube relative to the ultrasonic probe, or by selection of evacuation tubes of the desired length. Various embodiments are disclosed.

22 Claims, 3 Drawing Sheets

U.S. PATENT DOCUMENTS

| | | |
|---|---|---|
| 6,379,326 B1 | 4/2002 | Cimino |
| 6,428,499 B1 | 8/2002 | Halverson |
| 6,626,890 B1 * | 9/2003 | Nguyen et al. ............. 604/542 |
| 6,723,063 B1 * | 4/2004 | Zhang et al. ................. 604/22 |
| 6,761,701 B1 * | 7/2004 | Cucin .......................... 604/22 |
| 2001/0012922 A1 | 8/2001 | Cimino |
| 2002/0029054 A1 | 3/2002 | Rabiner et al. |
| 2002/0107446 A1 | 8/2002 | Rabiner et al. |

* cited by examiner

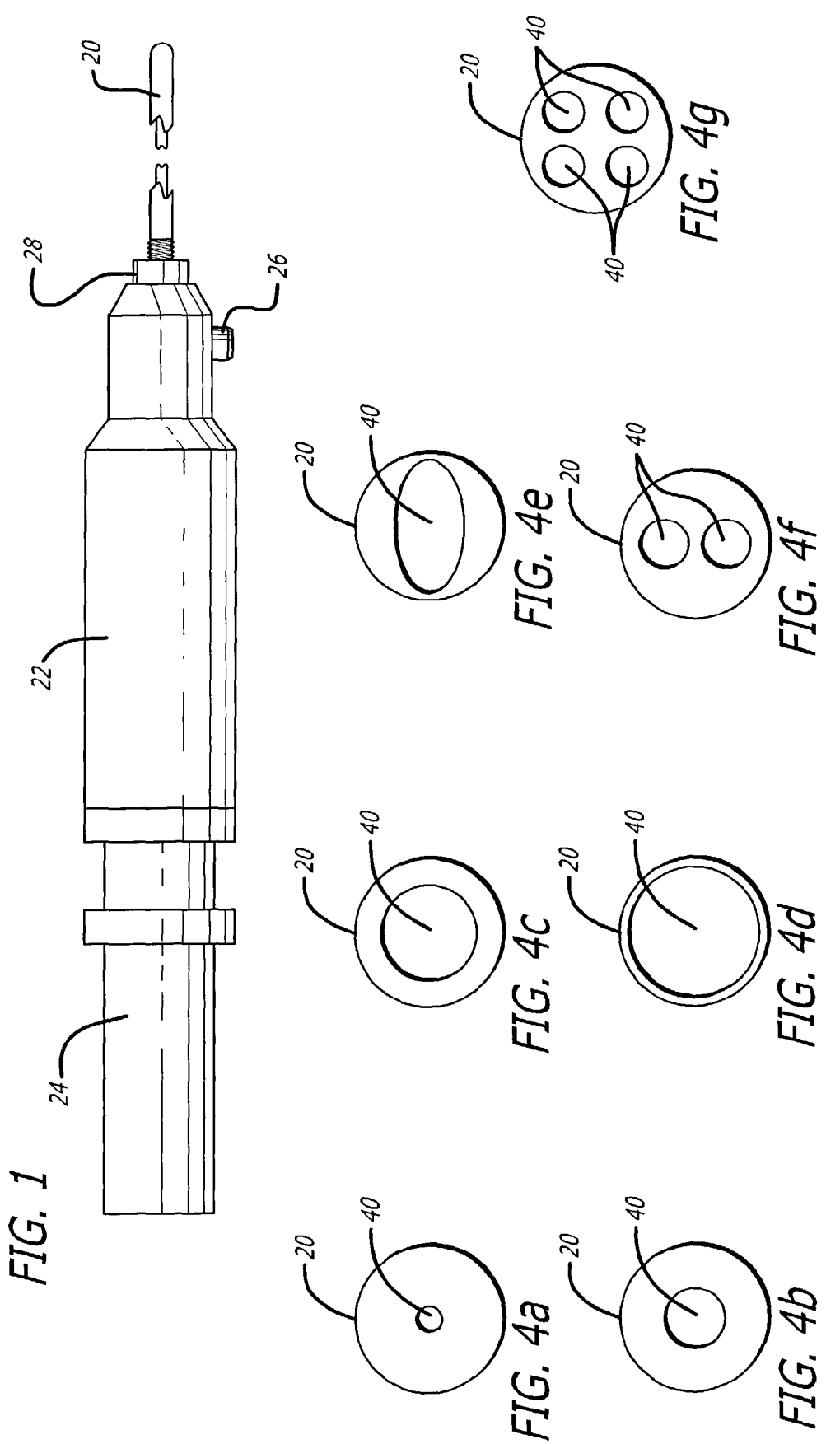

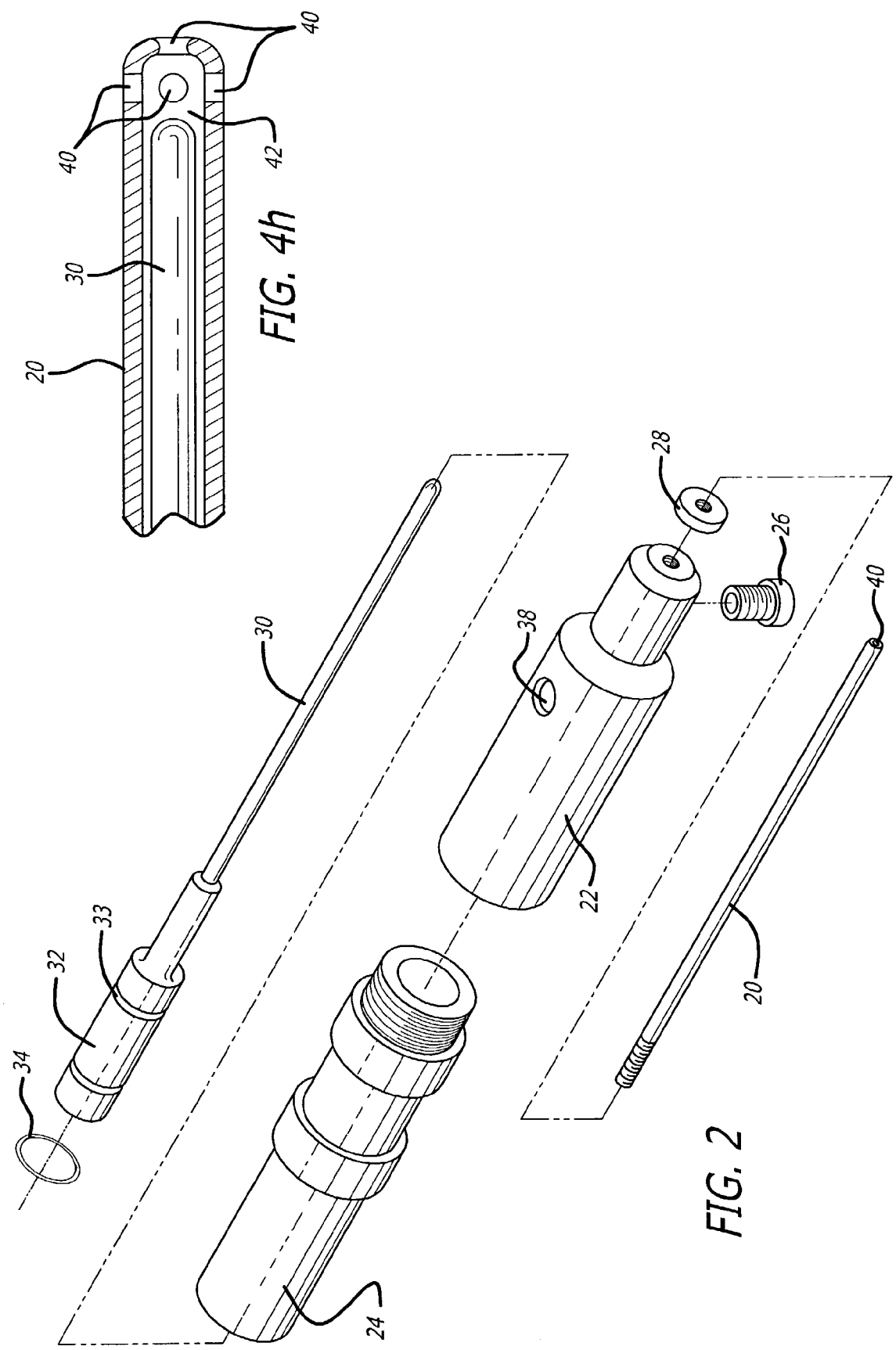

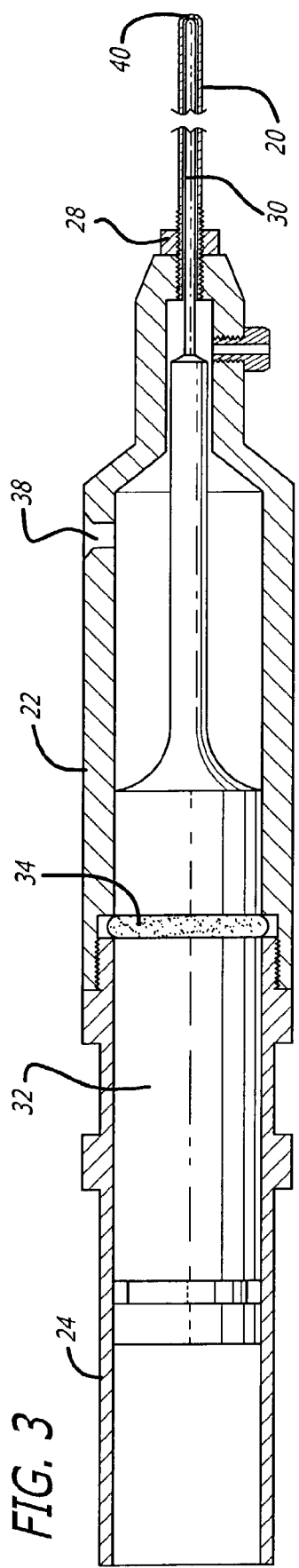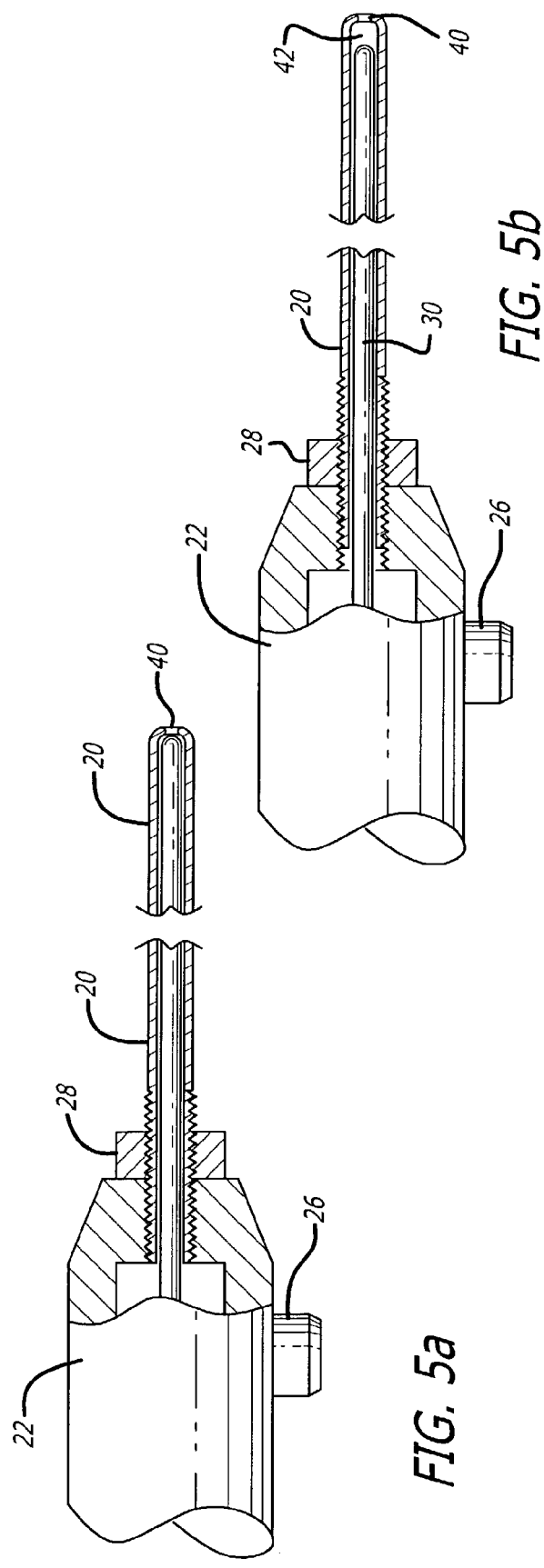

LIPOSUCTION DEVICES AND METHODS AND SURROUNDING ASPIRATION SYSTEMS AND METHODS

CROSS-REFERENCE TO RELATED APPLICATION

This application claims the benefit of U.S. Provisional Patent Application No. 60/337,045 filed on Nov. 8, 2001.

BACKGROUND OF THE INVENTION

1. Field of the Invention

The present invention relates to the field of ultrasound-assisted liposuction.

2. Prior Art

Various devices and methods for ultrasound-assisted liposuction are known in the art. Such devices include those described in U.S. Pat. Nos. 4,886,491, 5,123,903, 5,419,761, 5,514,086, 6,033,375, 6,270,471, 6,336,925, 6,368,299, 6,379,326 and 6,428,499 and U.S. patent application Publication Nos. 2001/0012922, 2002/0029054 and 2002/0107446.

In ultrasound-assisted liposuction, the object is to a use ultrasonic energy to liquefy body fat for substantially immediate extraction through some form of cannula. In some devices, the probe to which ultrasonic energy is applied itself forms the cannula, whereas in other devices, a separate sheath is provided over the probe to define an annular passage between the probe and sheath for extraction purposes and to isolate the proximal end and middle of the probe from the surrounding tissue. This is important, as otherwise the body entry point and nearby tissue would be constantly or at least repeatedly subjected to the ultrasonic energy and could be easily burned, even though the distal end of the probe were kept moving to avoid such problems at the distal end. In devices wherein the ultrasonic probe itself forms the cannula, resonant techniques can be applied to reduce probe ultrasonic vibration other than at the distal end thereof.

In any event, the object of such devices is the efficient removal of fat tissue from the body while avoiding, as much as possible, damage to surrounding tissue, blood vessels, and the like. The present invention has similar objects of safety and efficiency, as well as numerous other objects as shall become apparent from the disclosure herein, including but not limited to the incorporation of features making the safety and efficiency of the devices of the invention more dependent on the device itself rather than on the skill and experience of the operator.

BRIEF SUMMARY OF THE INVENTION

Liposuction devices and methods and surrounding aspiration systems and methods that reduce the chances of burning and necrosis. The devices include an evacuation tube surrounding an ultrasonic probe, including the distal end thereof to define a liquefaction and/or rupture chamber. The evacuation tube has one or more openings in the distal end through which tissue such as fatty tissue may enter for rupture/liquefaction therein. Containing the ultrasonic probe within the evacuation tube avoids any possible contact with surrounding tissue other than tissue that gets drawn into the liquefaction and/or rupture chamber. The size of the liquefaction and/or rupture chamber may be variable by adjustment of the axial position of the evacuation tube relative to the ultrasonic probe, or by selection of evacuation tubes of the desired length. Various embodiments are disclosed.

BRIEF DESCRIPTION OF THE DRAWINGS

FIG. 1 is a side view of one embodiment of ultrasonically assisted liposuction device in accordance with the present invention.

FIG. 2 is an exploded view of the embodiment of the ultrasonically assisted liposuction device of FIG. 1.

FIG. 3 is an side partial cross section of the embodiment of the ultrasonically assisted liposuction device of FIG. 1.

FIGS. 4*a* through 4*d* illustrate exemplary variations in size of the opening in the end of the evacuation tube.

FIG. 4*e* illustrates one possible variation in shape of the opening in the end of the evacuation tube.

FIGS. 4*f* and 4*g* illustrate multiple openings in the end of the evacuation tube.

FIG. 4*h* illustrates multiple openings in the end of the evacuation tube, including openings in the side wall of the distal end of the evacuation tube in fluid communication with the liquefaction and/or rupture chamber FIGS. 5*a* and 5*b* are partial cross sections illustrating the adjustability of the device for adjusting the size of the liquefaction and/or rupture chamber.

DETAILED DESCRIPTION OF THE PREFERRED EMBODIMENTS

In the description to follow, a preferred embodiment of the present invention and certain variations thereof will be described in detail. It is to be understood, however, that the description of certain variations is for illustration purposes only and is not intended to exclude other variations in the same or in other parts of the preferred embodiments disclosed.

First referring to FIG. 1, a side view of one embodiment of an ultrasonic surgical liposuction apparatus in accordance with the present invention may be seen. Visible in the apparatus of FIG. 1 is an evacuation tube 20, a forward handpiece 22 and a rear handpiece 24. Also visible in FIG. 1 is an aspiration conduit 26 configured to removably attach to an aspiration unit providing a suction thereon for removal of material from the evacuation tube 20. Finally, also visible in FIG. 1 is adjustment ring 28 that retains the evacuation tube 20 to the forward handpiece 22 at the desired axial position.

Now referring to FIGS. 2 and 3, an exploded view of the embodiment of the ultrasonically assisted liposuction device of FIG. 1 and a cross section thereof, respectively, may be seen. In the preferred embodiment, a solid probe 30 is used, though probes of other configurations, such as hollow probes, may also be used if desired. The probe 30 is coupled an ultrasonic vibration unit 32, typically a piezoelectric drive unit (which may be a conventional, commercially available unit). In general, such piezoelectric drive units, as well as probe design and construction itself, are well known in the prior art, and accordingly, design details of the probe 30 and ultrasonic vibration unit 32 need not be given herein.

The ultrasonic probe assembly of FIG. 2 fits within an outer assembly. The major parts of the outer assembly comprise the evacuation tube 20, the forward handpiece 22, the rear handpiece 24, the aspiration conduit 26 and the adjustment ring 28, all also visible in FIG. 1. An O-ring 34 fits between the forward handpiece 22 and the rear handpiece 24, and is operative within groove 33 of the body of the ultrasonic vibration unit 32.

Now referring specifically to FIG. 3, the ultrasonic vibration unit 32 has a slip fit within the front handpiece 22 and the rear handpiece 24, being axially located with respect thereto by the O-ring 34 trapped with respect to the front and rear handpieces in the region in which they couple together and trapped with respect to the ultrasonic vibration unit 32 in the O-ring groove 33 (FIG. 2) in which part of the O-ring resides. The O-ring also provides a seal, preferably but not necessarily a hermetic seal, to define a chamber 36 in fluid communication with vent hole 38, aspiration conduit 26 and the opening 40 in the distal end of the evacuation tube 20. In that regard, the opening 40 in the end of the evacuation tube is in communication with the aspiration conduit 26 by way of the annular clearance between the outer diameter of the ultrasonic probe 30 and the inner diameter of the evacuation tube 20. Also in fluid communication with the aspiration conduit 26 is the vent hole 38. In use, when the surgeon manually covers the vent hole 38, the suction on the aspiration conduit 26 encourages fat tissue into the liquefaction and/or rupture chamber 42 between the end of the probe and the evacuation tube, the liquefaction of the fat in the chamber, and the aspiration of fat out through the space between the probe and the evacuation tube and ultimately out through the aspiration conduit. When the vent hole 38 is not covered or occluded, air will flow through the vent hole between the ultrasonic vibration unit and the front handpiece to the aspiration conduit, so that there will not be any meaningful suction through the evacuation tube.

Now referring to FIGS. 4a through 4d, exemplary variations in size of the opening 40 in the end of the evacuation tube 20 may be seen. Since the evacuation tube is not a permanent part of the assembly, but may be easily removed and replaced with another evacuation tube, the surgeon may select the size of the opening that is found to most fit the surgeon's task and technique, either before the surgery or even during the surgery. In that regard, the shape of the opening does not necessarily have to be round, but could be of other shapes, such as oblong as shown in FIG. 4e, and orientable on the assembly as the surgeon desires. Also, more than one opening in the tip may be used, such as the two openings 40 of FIG. 4f, or the four openings 40 of FIG. 4g. Further, openings may also be provided along and/or along at least part of the length of the evacuation tube instead of or in addition to the opening or openings 40 in the distal end of the evacuation tube. By way of example, FIG. 4h also illustrates one opening 40 in the center of the distal end of the evacuation tube as well as four openings 40 at the side of the distal end in the region of the liquefaction and/or rupture chamber. One or more openings may also or alternatively be provided further along the length of the evacuation tube. In general, the edges of the opening or openings will preferably be well rounded in cross section, and usually but not necessarily always, the hole or opening in the end of the evacuation tube will have a smaller cross sectional area than the cross sectional of the internal diameter of the evacuation tube, and will be centered with respect to the axis thereof.

Referring now to FIGS. 5a and 5b, the adjustability of the size (length) of the liquefaction and/or rupture chamber 42 (the chamber between the end of the probe 30 and the evacuation tube 20 may be seen. As shown therein, the evacuation tube 20 threads into the forward handpiece, and is locked in position by lock ring 28. The threaded length of the evacuation tube into the forward handpiece 22 is sufficient to allow locking the tube into the forward handpiece with the lock ring at various axial extensions. By way of example, FIG. 5b illustrates the locking of the evacuation tube 20 at an extended position, thereby creating a liquefaction and/or rupture chamber 42 of substantial length. FIG. 5b illustrates the locking of the evacuation tube 20 at an unextended position, thereby creating a liquefaction and/or rupture chamber 42 of nearly zero length. This adjustment may be made by the surgeon to fit his particular needs and desires, and can even be adjusted during liposuction surgery as conditions may suggest.

With the evacuation tube in the position shown in FIG. 5b, the ultrasonic probe will still liquefy the fat tissue that enters the liquefaction and/or rupture chamber 42, but inadequate ultrasonic energy will escape the liquefaction and/or rupture chamber 42 to cause burning and necrosis of tissue surrounding even the distal end of the evacuation tube. This can have advantages for less experienced surgeons, or even highly experienced surgeons, as it allows dwelling at one location without burning and necrosis, or use of a slow motion as when sculpturing the fat removal for best cosmetic results. For faster bulk removal, a smaller (shorter) liquefaction and/or rupture chamber 42 might be used, perhaps with an evacuation tube 20 having a larger opening in the end of the evacuation tube. Still, even in this case, the likelihood of burning and necrosis is reduced in comparison to much of the prior art due to the fact that the probe will still only contact tissue that enters the evacuation tube.

While the adjustability of the present invention is provided by the threaded coupling of the evacuation tube 20 to the forward handpiece, other adjustable attachment mechanisms may be used, or as a further alternative, the adjustment by be made by selecting a specific evacuation tube for use from among a variety of evacuation tubes of differing lengths.

In use, the present invention normally uses a two stage procedure. First, the liquefaction and/or rupture chamber is wetted/infiltrated by fatty tissue, and then simultaneous aspiration, liquefaction, and rupture of fatty tissue proceeds. Once the process begins, it normally can be continued on a substantially continuous basis until completed. In that regard, the suction used for aspiration may be the same or similar to that used with other liposuction devices, and therefore may be provided by prior art equipment for that purpose. Aspiration may also be effectively provided by other means, such as by a syringe, by natural drainage or by a peristaltic pump, to name a few alternatives.

A preferred embodiment has been described herein with respect to use with an ultrasonic probe for liposuction purposes. However it is to be understood that other forms of energy might be used, such as, by way of one other example, radio frequency energy. Also the apparatus and methods of the present invention may be applied to the removal of solid tissue, such as, by way of example, organs, muscle or tumors, and even to some extramedical applications.

The following both summarizes and provides some preferred parameters:

The surrounding aspiration system of the preferred embodiment consists of two parts:
  a) an aspiration tube that surrounds an ultrasonic probe
  b) an encasing that surrounds an ultrasonic handpiece, in the preferred embodiment, a two piece encasing In a preferred embodiment, the aspiration tube is disposable (single-use). In an alternative embodiment, the aspiration tube can be reusable (multiple use), and can be sterilized by steam autoclave or other standard sterilization methods. The aspiration tube coaxially surrounds the ultrasonic probe along its entire shaft, extending beyond the distal tip of the ultrasonic probe. In a preferred embodiment, the ultrasonic probe is solid, though in alternative embodiments, the ultrasonic probe can be hollow. The ultrasonic probe can be made of titanium, titanium alloy, stainless steel, polymer, or other material, though in a preferred embodiment, the solid ultrasonic probe is made of a titanium alloy.

The proximal end of the aspiration tube is detachably connected to the encasing of the ultrasonic handpiece. The surrounding aspiration tube and the encasing of the ultrasonic handpiece can be made of polytetrafluoroethylene ("PTFE", e.g., Teflon®), polymer, or another nonmetallic or metallic material or materials, as desired. The material preferably used to produce the surrounding aspiration tube and ultrasonic handpiece encasing (e.g., polytetrafluoroethylene) has a low coefficient of friction, provides a thermal and kinetic insulation/barrier, has been demonstrated to be compatible with the titanium ultrasonic probe, and is biocompatible with the human body. Because of the low coefficient of friction, inadvertent deflection of the evacuation tube so that it touches the ultrasonic probe will not significantly reduce the ultrasonic energy reaching the tip of the probe, so that the liposuction process will not be interrupted by such deflection and touching.

The encasing of the ultrasonic handpiece contains a depressurization/collection chamber, depressurization hole, and a detachable aspiration connector to which suction can be applied. A flexible or O-ring hermetically seals the space between the inner surface of the encasing surrounding the ultrasonic handpiece and the outer surface of the portion of the ultrasonic handpiece containing the piezoelectric transducer assembly, proximal to the depressurization/collection chamber.

The space between the outer surface of the ultrasonic probe and the inner surface of the aspiration tube provides an aspiration conduit from the tip of the aspiration tube to the suction connector on the encasing of the ultrasonic handpiece. This space, the aspiration conduit, can range from 0.2 mm to 3 mm.

The depressurization hole is typically occluded by the user's finger to provide suction to the aspiration tube when suction is simultaneously applied to the aspiration connector on the encasing of the ultrasonic handpiece. The diameter of the depressurization hole preferably can range from 1 mm to 1.5 cm. The depressurization hole provides a passage between the inner surface of the liquefaction and/or rupture chamber and the outer surface of the ultrasonic handpiece encasing, so that the suction through the aspiration channel ceases immediately when the depressurization hole becomes unoccluded.

An opening at the distal tip of the aspiration tube provides ingress to fatty tissue that is liquefied and/or ruptured within the space located between the tip of the ultrasonic probe and the tip of the aspiration tube. The space located between the tip of the ultrasonic probe and the tip of the aspiration tube is referred to and acts as a liquefaction and/or rupture chamber. This chamber totally isolates the solid ultrasonic probe and tip from direct contact with structures surrounding subcutaneous fat (e.g., nerves, vessels, connective tissue, etc.) and the dermis, preventing risk of burns. Fatty tissue entering the liquefaction and/or rupture chamber is liquefied and/or ruptured within this chamber when ultrasonic energy is applied to the ultrasonic probe. The opening at the distal tip of the aspiration tube can be a circular, rounded, or non-circular shape whose edge has a curved and/or rounded radius (smooth, non-traumatic edges).

The distal portion of the aspiration tube containing the liquefaction and/or rupture chamber can be detachably connected to the main body of the aspiration tube, allowing exchange and/or replacement with liquefaction and/or rupture chambers containing different geometries and/or opening sizes. The distance between the distal tip of the ultrasonic probe and the distal tip of the aspiration tube is user-adjustable by adjusting or manipulating the length of the aspiration tube in a rotational, sliding, or other manner. This distance between the most distal point of the tip of the aspiration tube and the most distal point of the tip of the solid ultrasonic probe preferably can range from 0 to 1.5 cm.

The (adjustable) length of the aspiration tube chosen by the user can be secured using a threaded ring or other securing and/or locking mechanism. The total length of the aspiration tube can range from 1 mm to 50 cm, depending on the application and preferences of the user. The total length of the solid ultrasonic probe can also range from 1 mm to 50 cm.

The diameter of the hole located at the distal tip of the aspiration tube can range from 1 mm to 8 mm at its widest point. The outside diameter of the aspiration tube can range from 2 mm to 10 mm. The outside diameter of the solid ultrasonic probe can range from 1 mm to 8 mm at its tip (most distal point with respect to the ultrasonic handpiece).

Ultrasonic energy is applied to the ultrasonic probe by the ultrasonic handpiece to which the ultrasonic probe is detachably connected. In an alternative embodiment, ultrasonic energy may also be applied to the aspiration tube that surrounds the solid ultrasonic probe. In another alternative embodiment, other sources of energy can be applied to the probe and/or sleeve (e.g., laser, radio frequency, microwave, etc.). If ultrasonic energy is applied to the aspiration tube, it can be done so simultaneously or independently from ultrasonic energy applied to the solid ultrasonic probe.

The ultrasonic handpiece converts electrical energy supplied by the generator to mechanical energy (ultrasonic vibrations) via a piezoelectric transducer assembly located within the ultrasonic handpiece. The frequency and amplitude range of the ultrasonic probe and/or aspiration tube is typically in the range of 10 to 35 kHz and 0 to 300 microns. Alternative embodiments can range up to 50 kHz and 500 microns.

The liquefied and/or ruptured fatty tissue is aspirated through the aspiration channel of the aspiration tube, into the liquefaction and/or rupture chamber, and then immediately removed through the aspiration connector on the encasing of the ultrasonic handpiece. An external collector and/or container subsequently receives the liquefied and/or ruptured fatty tissue. The immediate removal of liquefied and/or ruptured fatty tissue from the liquefaction and/or rupture chamber prevents multiple, successive applications of ultrasonic energy to the same fatty tissue.

Thus disclosed herein are disposable aspiration tubes for use with an ultrasound assisted liposuction devices, and devices so equipped, that improve the safety and efficiency of liposuction procedures compared to traditional/suction-assisted liposuction or prior forms of ultrasound-assisted liposuction. This is achieved, at least in part, by confining the ultrasonic probe to within the evacuation tube in a manner and amount that achieves the desired liquefaction while so confining the ultrasonic energy as to avoid burns and necrosis from excessive exposure of surrounding tissue to the ultrasonic energy.

The technique and technology of this invention can also be adapted for use in non-clinical applications, and/or other clinical applications such as ophthalmology, neurology, liver/hepatic, gynecology, urology, otorhinolaryngology and general surgery, to name a few.

The invention and method has numerous advantages compared to traditional/suction-assisted liposuction and prior forms of ultrasound-assisted liposuction, including:

Increased patient safety (minimizes risk of skin burns and skin necrosis).

Patient safety is ensured even during long or static application of ultrasonic energy.

Higher efficiency compared to existing liposuction techniques, including ability to remove/aspirate large volumes of fatty tissue in a single session (3 liters to 10 liters).

Higher tissue specificity, targeted at subcutaneous fat.

Less vascular trauma and/or bleeding/blood loss.

Little or no injury to structures surrounding fat, including vessels, nerves, and connective tissue.

Greater ability to safely treat superficial tissue layers (closer to skin surface), providing improved skin contraction/retraction/tightening.

Ability to safely and effectively treat a greater number of anatomical areas in the patient's body improves sculpturability and desired aesthetic results.

Simultaneous evacuation of the majority of possible free radical production.

Decreased surgeon fatigue.

Minimal noise and vibration.

Reduced total operative time compared to traditional/suction assisted liposuction ("SAL") and prior forms of ultrasound-assisted liposuction.

Short surgeon learning curve.

The foregoing description is intended to be illustrative only and not by way of limitation of the invention, as numerous further alternative embodiments in accordance with the invention will be apparent to those skilled in the art. Thus while certain preferred embodiments of the present invention have been disclosed herein, it will be obvious to those skilled in the art that various changes in form and detail may be made in the invention without departing from the spirit and scope of the invention as set out in the full scope of the following claims.

What is claimed is:

1. An adapter for use with an ultrasonic vibrator having an ultrasonic probe thereon, the probe having a proximal end coupled to the ultrasonic vibrator and a distal end, comprising;

a handpiece assembly to fit over and locate with respect to the ultrasonic vibrator, the handpiece assembly having a seal to seal with respect to the ultrasonic vibrator and probe to define a first fluid chamber adjacent the proximal end of the ultrasonic probe between the handpiece assembly and an ultrasonic vibrator, the handpiece assembly having an aspiration conduit coupled thereto for fluid communication with the first chamber and adapted for connection to an aspiration unit, the handpiece assembly also having a depressurization opening in fluid communication with the first chamber for controllably venting the first chamber;

an evacuation tube coupled to the handpiece assembly and extending over the ultrasonic probe therein, including the distal end of the ultrasonic probe therein, the evacuation tube being adapted to define a fluid passageway between the evacuation tube and a probe therein, which fluid passageway is in fluid communication with the first chamber;

the space between the end of the probe and the end of the evacuation tube defining a second chamber, the evacuation tube having at least one opening in the distal end thereof in fluid communication with the second chamber.

2. The adapter of claim 1 wherein the second chamber is a chamber for liquefaction and/or rupture of fat tissue.

3. The adapter of claim 1 wherein the distal end of the evacuation tube is rounded with an opening in the center thereof.

4. The adapter of claim 3 wherein the coupling of the evacuation tube to the handpiece assembly is adjustable to provide an adjustment of the distance between the end of the probe and the end of the evacuation tube.

5. The adapter of claim 4 wherein the evacuation tube is threaded to the handpiece assembly, whereby the distance between the end of the probe and the end of the evacuation tube may be adjusted by rotation of the evacuation tube relative to the handpiece assembly.

6. The adapter of claim 4 wherein the opening in the distal end of the evacuation tube is round.

7. The adapter of claim 4 wherein the opening in the distal end of the evacuation tube is oblong.

8. The adapter of claim 4 wherein the evacuation tube is a polytetrafluoroethylene evacuation tube.

9. The adapter of claim 8 wherein the handpiece assembly is polytetrafluoroethylene.

10. The adapter of claim 1 wherein the handpiece assembly is a two piece assembly.

11. The adapter of claim 1 wherein the evacuation tube has a plurality of openings in the distal end thereof in fluid communication with the second chamber.

12. An ultrasonic assisted liposuction device comprising:

an ultrasonic vibrator having an ultrasonic probe thereon, the probe having a proximal end coupled to the ultrasonic vibrator and a distal end;

a handpiece assembly to fit over and locate with respect to the ultrasonic vibrator, the handpiece assembly having a seal to seal with respect to the ultrasonic vibrator and probe to define a first fluid chamber adjacent the proximal end of the ultrasonic probe between the handpiece assembly and an ultrasonic vibrator, the handpiece assembly having an aspiration conduit coupled thereto for fluid communication with the first chamber and adapted for connection to an aspiration unit, the handpiece assembly also having a depressurization opening in fluid communication with the first chamber for controllably venting the first chamber;

an evacuation tube coupled to the handpiece assembly and extending over the ultrasonic probe therein, including the distal end of the ultrasonic probe therein, the evacuation tube being adapted to define a fluid passageway between the evacuation tube and a probe therein, which fluid passageway is in fluid communication with the first chamber;

the space between the end of the probe and the end of the evacuation tube defining a second chamber, the evacuation tube having at least one opening in the distal end thereof in fluid communication with the second chamber.

13. The adapter of claim 12 wherein the second chamber is a chamber for liquefaction and/or rupture of fat tissue.

14. The adapter of claim 12 wherein the distal end of the evacuation tube is rounded with an opening in the center thereof.

15. The adapter of claim 14 wherein the coupling of the evacuation tube to the handpiece assembly is adjustable to provide an adjustment of the distance between the end of the probe and the end of the evacuation tube.

16. The adapter of claim 15 wherein the evacuation tube is threaded to the handpiece assembly, whereby the distance between the end of the probe and the end of the evacuation tube may be adjusted by rotation of the evacuation tube relative to the handpiece assembly.

17. The adapter of claim 15 wherein the opening in the distal end of the evacuation tube is round.

18. The adapter of claim 15 wherein the opening in the distal end of the evacuation tube is oblong.

19. The adapter of claim 15 wherein the evacuation tube is a polytetrafluoroethylene evacuation tube.

20. The adapter of claim 19 wherein the handpiece assembly is polytetrafluoroethylene.

21. The adapter of claim 12 wherein the handpiece assembly is a two piece assembly.

22. The adapter of claim 12 wherein the evacuation tube has a plurality of openings in the distal end thereof in fluid communication with the second chamber.

* * * * *